US007208166B2

(12) United States Patent
Marchini et al.

(10) Patent No.: US 7,208,166 B2
(45) Date of Patent: Apr. 24, 2007

(54) USE OF BOTULINE TOXIN TO OBTAIN A PRODUCT TO BE USED IN ARTICULAR PATHOLOGIES, PARTICULARLY COXARTHROSIS, EPICONDYLITIS AND ROTATOR MUSCLE CAP PATHOLOGY

(75) Inventors: Corrado Marchini, Coseano (IT); Fabiano Pinat, Udine (IT); Fabio Pinat, Udine (IT); Francesca Zecchini, Udine (IT)

(73) Assignee: Societe de Conseils de Recherches et d'Applications Scientifiques SAS, Paris (FR)

( * ) Notice: Subject to any disclaimer, the term of this patent is extended or adjusted under 35 U.S.C. 154(b) by 0 days.

(21) Appl. No.: 10/250,486

(22) PCT Filed: Jan. 4, 2002

(86) PCT No.: PCT/IB02/00003

§ 371 (c)(1),
(2), (4) Date: Nov. 14, 2003

(87) PCT Pub. No.: WO02/053175

PCT Pub. Date: Jul. 11, 2002

(65) Prior Publication Data

US 2004/0071735 A1 Apr. 15, 2004

(30) Foreign Application Priority Data

Jan. 5, 2001 (IT) .............................. UD01A0002

(51) Int. Cl.

*A61K 39/02* (2006.01)
*A61K 39/08* (2006.01)
*A61K 38/00* (2006.01)
*G01N 31/00* (2006.01)

(52) U.S. Cl. ............................... 424/236.1; 424/234.1; 424/239.1; 424/247.1; 436/8; 436/18; 514/2

(58) Field of Classification Search ..................... None
See application file for complete search history.

(56) References Cited

U.S. PATENT DOCUMENTS

| | | | | |
|---|---|---|---|---|
| 6,063,768 | A * | 5/2000 | First | 514/14 |
| 6,395,277 | B1 | 5/2002 | Graham | |
| 6,458,365 | B1 * | 10/2002 | Aoki et al. | 424/239.1 |
| 6,464,986 | B1 * | 10/2002 | Aoki et al. | 424/239.1 |
| 6,869,610 | B2 | 3/2005 | Aoki et al. | |
| 7,091,176 | B2 | 8/2006 | Aoki et al. | |
| 2002/0176872 | A1 | 11/2002 | Aoki et al. | |

FOREIGN PATENT DOCUMENTS

| | | |
|---|---|---|
| WO | 93 05800 | 4/1993 |
| WO | 95 17904 | 7/1995 |
| WO | 0015245 | 3/2000 |

OTHER PUBLICATIONS

Robertsson et al (Journal of Arthroplasty, Oct. 1995, vol. 10. No. 5, p. 632-635).*

Williams & Wilkins, Stedman's Medical Dictionary, 26th Edition, Illustrated in Color, 1995, p. 988.

Gracies et al., *Neurologist* 2000, 6(2), "Botulinum Toxin Therapy", pp. 98-115.

Kessler et al., *Neurologist Toxicology* 1997, 18(3), "Botulinium Toxin: From Poison to Remedy", pp. 761-770.

Montecucco et al., *Mol Microbiol*, 1994, 13(1), Mechanism of Action of Tetanus and Botulinum Neurotoxins, pp. 1-8.

Polo et al., *Mov Disord* 1994, 9 (suppl. 1), "Botulinum Toxin A and Rigidity", p. 84.

Boyd et al., *European Journal of Neurology* 1999, 6 (suppl. 4), "Objective Measurement of Clinical Findings in the use of Botulinum Toxin Type A for the Management of Children With Cerebral Palsy", pp. S23-S35.

Boyd et al., *European Journal of Neurology* 1999, 6 (suppl. 4), Medium-Term Response Characterisation and Risk Factor Analysis of Botulinum Toxin Type A in the Management of Spasticity in Children With Cerebral Palsy, pp. S37-S45.

Boyd et al., *Dev Med Child Neurol* Aug. 1998, 40 (suppl. 78), "Session I: Botox", pp. 28-29.

G. Jenkins and W. Hartung, The Chemistry of Organic Medicinal Products, Moscow, p. 420 (1949).

BOTOX© product entry; "Neuromuscular Agents", 2000 Mims Annual, pp. 5-433 to 5-434.

Gasser et al.; "Botulinum Toxin a in Orthopaedic Surgery", The Lancet, Sep. 21, 1991; vol. 338 (8769); p. 761.

Morre et al.; "Treatment of Chronic Tennis Elbow With Botulinum Toxin"; *The Lancet* Jun. 14, 1997; vol. 349 (9067); p. 1746.

Placzek et al.; "Therapy for Chronic Radial Epicondylitis With Botulinum Toxin A - A Therapy Trial with a 2-Year-Follow-Up", Z Orthop Ihre Grenzgeb; Nov.-Dec. 2004; 142(6); p. 701-705 (Reference with Abstract in English).

S.M. Wong et al., "Treatment of Lateral Epicondylitis With Botulinum Toxin. A Randomized, Double-Blind, Placebo-Controlled Trial", Summaries for Patients; Annals of Internal Medicine; Dec. 6, 2005; 143(II); pp. 148, 793-797, and W-161.

Abstract of AU 15162/95, published Jul. 17, 1995.

Abstract of AU 25664/92, published Apr. 27, 1993.

* cited by examiner

*Primary Examiner*—Nita Minnifield
*Assistant Examiner*—Vanessa L. Ford
(74) *Attorney, Agent, or Firm*—Stevens, Davis, Miller & Mosher, LLP

(57) ABSTRACT

Use of botulin toxin to obtain a product intended to be administered intramuscular with lissive effect in treating articular pathologies, particularly coxarthrosis, or arthrosis of the hip, epicondylitis of the elbow and rotator muscle cap pathology of the shoulder.

6 Claims, No Drawings

USE OF BOTULINE TOXIN TO OBTAIN A PRODUCT TO BE USED IN ARTICULAR PATHOLOGIES, PARTICULARLY COXARTHROSIS, EPICONDYLITIS AND ROTATOR MUSCLE CAP PATHOLOGY

FIELD OF THE INVENTION

The invention refers to the use of botulin toxin to obtain a product to be used in articular pathologies connected with muscular tensions and contractions, particularly coxarthrosis, or arthrosis of the hip, epicondylitis of the elbow, or rotator muscle cap pathology relating to the periarticular structures of the shoulder.

BACKGROUND OF THE INVENTION

In the state of the art, the name arthrosis is meant as a chronic degenerative arthropathy which primarily affects the articular cartilage and secondly the bone, synovial and capsular component. The progressive rise in the average age of the population and the evolving and disabling character of the disease have together contributed to make arthrosis one of the most frequent diseases, with the greatest impact on society.

To be more exact, due to the continuous stresses to which they are subject, the joints are frequently subject to arthrosis. Arthrosis of the hip, or coxarthrosis, can also be caused by congenital and acquired deformities. Arthrosis causes pain in the region of the joint, for example in the hip, which characteristically refers to the level of the groin, radiates to the thigh, and is alleviated with rest. Hereafter, we shall describe the case of the hip joint, but the description can equally well be transferred to other cases of possible application according to the invention.

Sometimes the symptomatology of arthrosis of the hip can be manifested with a painful contracture of some muscles in the thigh. The functional limitation of coxarthrosis is of considerable importance given the importance this joint has in the actions of everyday life.

In the last twenty years, the surgical treatment of coxarthrosis has had a rapid and substantial evolution, with the introduction of total arthro-prosthesis of the hip. The immediate results obtained, compared with previous techniques, for example Voss's operation, or osteotomy of the femur and/or pelvis, have caused a new and—for many people—definitive course in the treatment of coxarthrosis.

In fact, before the arrival of arthro-prostheses, one of the operations most commonly practised, as proposed by Voss in 1952, included the surgical lysis of the most important periarticular muscles of the hip contractured in the course of the coxarthrosis, thus achieving the purpose of interrupting, in an efficient and enduring manner, the vicious circle created by the combination of pain-contracture and contracture-pain.

In practice, the operation proposed by Voss consisted in sectioning several groups of muscles which make up the muscular funnel of the hip; this sectioning caused, with immediate effect, a recovery in the travel of the hip and, when the patient awoke, the pain disappeared more or less completely. However, given the traumatic and detrimental nature of the operation, the introduction of a hip arthro-prosthesis has progressively replaced this practice and in recent years has been affirmed as the most efficient technique for restoring a damaged or degenerated joint.

However, even adopting the arthro-prosthesis has not completely solved the problem connected with coxarthrosis, especially considering the fact that prostheses used at present have an average duration of not more than 10–15 years, which means often the requirement of an operation to remove the old prosthesis and put a new one in. Such operations are often very complicated, especially when there is a clinical condition which is already problematic, for example in very elderly people. It is therefore necessary to delay as long as possible the fitting of any hip prosthesis, and yet at the same time to ensure that, while waiting for the operation, the patient can enjoy a high quality of life, absence of pain and efficient articulation.

Epicondylitis, instead, is an insertional tendinopathy with an acute or chronic course, which affects the proximal tendinous insertion of the muscles with an epicondyloid origin (the anconeus, the common extensor muscle of the fingers, extensor muscle of the little finger, the ulnar extensor of the wrist).

The causes of this condition are functional stresses and repeated traumas.

The symptomology is characterized by pain in the insertion seat of the tendon at the epicondyle.

The conservative therapeutic treatment consists of local infiltrations of painkillers or cortisone; when the infiltration therapy does not solve the symptoms of pain, a surgical treatment is normally started which consists of partly detaching the epicondyle muscles in order to reduce the tension in the tendinous insertion seat of the muscles involved.

On the contrary, rotator muscle cap pathology means the whole pathology, painful but not traumatic, of the periarticular structures of the shoulder. Most of these syndromes mainly refer to a tendinosis of the extrarotator muscles of the shoulder, and particularly to tendinosis of the supraspinal in the section below the acromion-clavicular arch; however it can involve the other extrarotator muscles (infraspinal, subspinal and teres minor).

The rotator muscle cap pathology is a tendinopathy which tends to occur in subjects who are over forty, or in young people who practised sports which entail a great effort in the upper limb.

The symptomology is differentiated: acute and chronic. Acute symptomology is usually the consequence of an effort and is accompanied by a serious functional limitation of the scapular-humeral joint.

The chronic form is characterized by recidivous forms of pain, it tends to become more accentuated both with abduction and with intra-extrarotation and can be referred to the friction produced; for this reason it is also called "impingement syndrome".

The treatment does not require a surgical operation in the acute forms and in its first approach to the chronic forms; it consists of local infiltration of cortisones and anaesthetics, followed by intense physio-kinesitherapy, both active and passive.

In friction syndromes it is appropriate to section off the coraco-acromial ligament with removal of the bursa and acromionplastic.

All the pathologies indicated above have in common the presence of a muscular tension which leads some contracted muscles to exert a pressure on the relative joint (hip, elbow, shoulder), accentuating the feeling of pain and causing a rapid degeneration of the phenomena of arthrosis of the joint itself.

At present, as we said, these pathologies are resolved mainly through surgery, by sectioning the muscles, or by intervening with prostheses or similar, or with the other treatments we have indicated.

The present Applicant has devised and embodied this invention to overcome the shortcomings of current techniques, and to obtain further advantages as explained hereafter.

SUMMARY OF THE INVENTION

The invention is set forth and characterized in the main claim, while the dependent claims describe other innovative characteristics of the main embodiment.

The purpose of the invention is to achieve a product suitable to solve, with a non-invasive method, articular pathologies, particularly coxarthrosis, epicondylitis and rotator muscle cap pathology. This product allows to avoid a surgical operation to section the muscle, or use polluting substances such as cortisone, and to delay as long as possible the application of a prosthesis in order to prevent the need for further replacement operations. Another purpose is to use the product according to the invention so as not to cause discomfort and side effects in the patient, so that the product can easily be used without requiring hospitalization and without the need for particular equipment, and will also be relatively low cost.

The invention provides to use botulin toxin as a basic substance, whether it be type A, B, C, D, E, F or G, and which has the capacity to intervene at muscular level exerting a de-contracting and progressively lissive effect.

To be more exact, the Applicant has discovered that, used at muscular level, the product according to the invention allows to act on the muscular contracture consequent to coxarthrosis, or other pathology deriving from muscular contracture.

In the specific case of coxarthrosis, the Applicant has verified that the periodic injection of the product to the long adductor muscle and/or the great adductor muscle, the iliopsoas or tensor muscle of the fascia lata, causes a drastic reduction in the pressure exerted by the femoral head against the natural seat, or cotyl, in the hip; this reduction allows a substantially immediate restoration of maximum travel to the hip, with considerable benefits in the autonomous mobility of the joint and a reduction in pain.

The basis of this intuition lies in the fact that the hip joint is subjected to an intermittent static pressure and a permanent muscular pressure. The entity of the muscular contracture on the articular surfaces is accentuated in particular pathological conditions, when the agonist and antagonist muscles come into play simultaneously (in the case of coxarthrosis both the pelvi-trochanter muscles and also the adductor muscles).

Consequently, in a patient affected by coxarthrosis, the femoral head is pressed against the cotyl by a dis-proportionate weight compared with its already undermined capacity to resist; when the hip is concerned, therefore, arthrosis assumes a brutal evolution, extremely painful and hence highly disabling.

The use of the product according to the invention, injected at muscular level, thus allows to reduce the effort of the muscle concerned, lessening the hyperactivity of the muscles which, if over-active, reduce the possibility of movement determined by the other agonist or antagonist muscles, thus making movement more physiological. Similarly, the reduction of muscular activity diminishes or abolishes the symptoms of pain, in the case of spasms or painful contractures.

In the case of epicondylitis, the use of the product according to the invention shares the same basic theory as the surgical operation, aiming to eliminate muscular tension in the insertion seat. This use provides to infiltrate the product according to the invention, with a possible electromyographic support, into the epicondyloid muscles involved.

On the contrary, in the case of rotator muscle cap pathology, the use of the product according to the invention is based on the de-contracturing action of the toxin applied, with an electromyographic support, to the rotator muscles involved, which on most occasions is the supraspinal, with the aim of eliminating muscular tension in the insertion seat; this use causes an increase in the subacromial space and allows a better rehabilitation.

According to the invention, all the subtypes of toxins (A, B, C, D, E, F and G) can be used to make the product according to the invention.

The use of the product according to the inventive idea of this invention is completely new and could not be foreseen from the vast previous experience.

Its de-contracturing effect develops in three main steps: connection with the specific presynaptic receptors, internalization, and toxic activity.

The product according to the invention blocks peripheral cholinergic transmission, preventing the acetylcholine from being released into the synaptic space and hence from linking with the cholinergic postsynaptic receptors. Irrespective of the size of the muscle, the use of the product according to the invention is supported, in many cases, by using an electromyographic guide, which improves the precision of the injection sites.

In the use for coxarthrosis, epicondylitis and rotator muscle cap pathology according to the invention, it has been verified that the effective dosage is individual and varies in proportion to the muscle mass to be treated; sometimes, moreover, given the considerable dimensions, several injections can be made in different places. The appearance of the benefits is subjective too: in some patients after a few hours, in others even after a week. It is also important to underline that the efficacy of this inventive idea has a limited duration, on average not more than three months.

According to the invention, the product uses a botulin toxin as a basic substance which cooperates with human albumin, and other aggregates; these aggregates depend on the type of toxin and the methods of extraction. These other aggregates can be sodium-based compounds, lactose and/or others, such as for example hydrochloric acid.

The whole is diluted with a physiological solution having sodium chloride to values comprised between g 0.45% and 1.0%, advantageously 0.9%.

The quantity of physiological solution is determined according to the type of botulin toxin and according to the type of aggregates, this type being determined by the type of extraction process employed.

In the following description we describe the use of the product in the case of coxarthrosis. We indicate the quantity of botulin toxin which has to be present, on average, in the product in order to obtain the desired result in the use thereof.

Hereafter, for the examples, we shall use a type of botulin toxin according to its commercial name, that is to say the type A toxin called Dysport (trade mark registered by IPSEN PHARMACEUTICALS Ltd., Dublin, Ireland). The type A toxin called BOTOX has also be experimented (trade mark registered by ALLERGAN Inc., Irvine, Calif., USA). It is within the spirit of the invention to use for example a type B botulin toxin known commercially as MYOBLOC (trade mark registered by ELAN PHARMACEUTICALS INC., South San Francisco, Calif., USA). It is also within the spirit of the invention to use botulin toxins type A, B, C, D, E, F or G of different provenance.

The use of the product according to the invention to treat coxarthrosis was tested on. 10 subjects, 6 women and 4 men, between the ages of 49 and 77 (average age 66.4) waiting for a hip prosthesis operation.

All the patients (Table 1) were subjected to a local injection of the product at the level of the great adductor muscle and the long adductor muscle, by means of a syringe connected to a Teflon-coated cannula connected by a monopolar method to an electromyographic apparatus.

In the following description, the quantities of toxin present in the product administered to the patients shall refer to the units of measurement of the Dysport toxin, since the unit of measurement of the Botox toxin is different. It should be noted that the various botulin toxins of various provenance and type have different operating characteristics, but their use comes within the spirit of the invention since the dosage needed to obtain the product is the result of a simple comparison.

Generally speaking, we can say that 50 MU Dysport correspond to about 7.5 MU Botox.

According to the invention, the basic dose of the botulin toxin needed to obtain the product according to the invention is comprised between 25 and 100 MU Dysport. We believe that the typical basic dose is 50 MU of the Dysport type toxin.

It is within the spirit of the invention to use products with one or more basic doses.

It is also within the spirit of the invention to use one or more products each having the basic dose.

EXAMPLES

TABLE 1

| Subjects | Age | Sex | BoNT/A dosage | Zone treated |
|---|---|---|---|---|
| 1 | 49 | F | 400 MU Dysport | Long adductor muscle |
| 2 | 56 | F | 200 MU Dysport | Long adductor muscle |
| | | | 50 MU Dysport | Great adductor muscle |
| 3 | 61 | M | 200 MU Dysport | Long adductor muscle |
| | | | 50 MU Dysport | Great adductor muscle |
| 4 | 64 | F | 200 MU Dysport | Long adductor muscle |
| | | | 50 MU Dysport | Great adductor muscle |
| 5 | 66 | M | 200 MU Dysport | Long adductor muscle |
| | | | 50 MU Dysport | Great adductor muscle |
| 6 | 69 | F | 150 MU Dysport | Long adductor muscle |
| | | | 100 MU Dysport | Great adductor muscle |
| 7 | 73 | M | 200 MU Dysport | Long adductor muscle |
| | | | 50 MU Dysport | Great adductor muscle |
| 8 | 73 | M | 200 MU Dysport | Long adductor muscle |
| | | | 50 MU Dysport | Great adductor muscle |
| 9 | 76 | F | 200 MU Dysport | Long adductor muscle |
| | | | 50 MU Dysport | Great adductor muscle |
| 10 | 77 | F | 200 MU Dysport | Long adductor muscle |
| | | | 50 MU Dysport | Great adductor muscle |

In the experiments, in order to obtain both subjective and objective data, we decided to make a standard objective examination of the hip where the extension was not evaluated, since this is always compromised from the very beginning of coxarthrosis, and a test to specifically evaluate the functionality thereof by means of the Harris Scale (Table 2).

The patients were examined before using the product and in two subsequent check-ups, respectively after 1 week and 3 months. In pre-use we evaluated the objectivity and functionality, in the check-up after 1 week functionality only and in the check-up after 3 months again objectivity and functionality. 8 patients (2–5, 7–10) were injected with the product, containing 200 MU of Dysport toxin, at the level of the long adductor muscle and 50 MU in the great adductor muscle; 1 patient (6) with 150 MU in the long adductor and 100 MU in the great adductor; 1 patient (1) with 400 MU in the long adductor.

The different dosages of toxin in the product, used in the last two cases were motivated by the attempt to define empirically the optimum dosage, according to the type of patient, to be used in the solution of this pathology. To obtain the best possible precision, all the injections were made with an electromyographic guide. Moreover, every patient was advised to do daily stretching exercises of the adductor muscles for one week, with leg stretched, for about 10 seconds, repeated 5 times, and 20 minutes on the exercise bike, to encourage the spread of the toxin in the muscle tissue.

TABLE 2

| EVALUATION OF THE HIP |
|---|
| HARRIS POINTS |
| NAME SURNAME AGE |
| PAIN IN HIP LIMP |
| (44) no (11) no |
| (40) slight, occasional (8) slight |
| (30) average (5) moderate |
| (20) moderate (0) severe |
| (10) severe |
| (0) continuous |
| SUPPORTS SITTING |
| (11) no (5) comfortable on any chair |
| (7) stick for long walks (3) comfortable on high chair |
| (5) stick for long time (0) not comfortable on any chair |
| (3) two sticks |
| (2) one crutch |
| (0) two crutches |
| (0) unable to walk |
| DISTANCE ABLE TO COVER STAIRS |
| (11) unlimited |
| (4) normally without banisters |
| (8) six blocks (500–1000 m) |
| (2) normally with banisters |
| (5) two, three blocks (500 m) |
| (1) helps himself in any way |
| (2) only in the house (0) unable |
| (0) in bed, sitting |
| SHOES AND SOCKS PUBLIC TRANSPORT |
| (4) easily (1) able to use public transport |
| (2) with difficulty (0) unable to use public transport |
| (0) with difficulty |
| ABSENCE OF DEFORMITY |
| (4) If patient has: |
| TOTAL POINTS . . . |
| A: < 30° continuous during flexion |
| B: < 10° contracture during adduction |
| C: < 10° contracture rot. int. in ext. |
| D: heterometry < 3.2 cm. |

According to the improvements seen in the objective examination, the results were sub-divided into the individual items of which it consists:

I) Normal Travel Values during Hip Flexion: from 0° to 135°
Average value pre-use: 103.3° (range 85°–120°).
Average value post-use: 115° (range 100°–130°).
Improvement in average values: 11.7°.
Condition unchanged: 4 patients.

II) Normal Travel Values during Hip Abduction: from 0° to 45–50°
Average value pre-use: 31° (range 0°–40°).
Average value post-use: 36.5° (range 0°–45°).
Improvement of values: 5.5°.
Condition unchanged: 4 patients.

III) Normal Travel Values during Hip Adduction: from 0° to 20°–30°
Average Value pre-Use: 6° (Range 0°–25°).
Average value post-use: 14.5°(range 0°–30°).
Improvement in average values: 8.5°.
Condition unchanged: 3 patients.

IV) Normal Travel Values during Hip Extrarotation: from 0° to 45°
Average value pre-use: 31° (range 0°–45°).
Average value post-use: 36.2° (range 5°–45°).
Improvement in average values: 5.2°.
Condition unchanged: 4 patients.

V) Normal Travel Values during Hip intrarotation: from 0° to 35°
Average Value Pre-Use: 13° (Range 0°–25°).
Average Value Post-Use: 20° (Range 0°–35°)
Improvement in Average Values: 7°.
Condition Unchanged: 4 patients.

VI) Normal Travel Values during Hip Flecto-Abduction: from 0° to 70°
Average value pre-use: 33.5° (Range 5°–45°).
Average value post-use: 43° (Range 5°–60°).
Improvement in average values: 9.5°.
Condition unchanged: 2 patients.

VII) Normal Travel Values during Hip Flecto-Adduction: from 0° to 30°
Average value pre-use: 7° (range 0°–20°).
Average value post-use: 11° (range 0°–20°).
Improvement in average values: 4°.
Condition unchanged: 5 patients.

VIII) Normal Values of Harris Scale between 0° and 107°
Average value pre-use: 55.4° (range 27°–83°)
Average value after 1 week: 82.6° (range 48°–104°)
Average value after 3 months: 79.4°(range 57°–103°)

It was thus possible to show experimentally that the use of the product according to the invention, based on botulin toxin, allows to delay the need for a hip prosthesis and to improve the quality of life for patients waiting for the operation, even though hip surgery remains, in any case, the preferred treatment in coxarthrosis therapy.

The use proposed is a reversible and "non-invasive variant" of the surgical approach, which allows to integrate the surgical therapy used today, reducing the use of painkillers, delaying the age at which the operation is performed and improving the patient's quality of life while he is waiting, which in many cases is a long time.

In the following claims we refer to the use of the type A Dysport botulin toxin to obtain the product according to the invention, since the identification of the basic unit dosage to obtain the product according to the invention is the result of a simple comparison of the characteristics of the other toxins, both type A toxins and also types B, C, D, E, F and G.

The invention claimed is:

1. A method for treating the symptom of endo-articular pressure in a patient suffering from coxarthrosis, comprising administering a botulinum toxin type A composition into a thigh muscle of said patient, wherein said thigh muscle is selected from at least one member of the group consisting of the long adductor muscle, great adductor muscle, iliopsoas and tensor muscle of the fascia lata, wherein said composition comprises a mixture of botulinum toxin type A and a physiological solution containing between 0.45% and 1.0% sodium chloride, and wherein said endo-articular pressure exerted by said thigh muscle on the femoral head against the cotyl in the hip is reduced.

2. The method according to claim 1, wherein said intramuscular administering of the composition is guided with an electromyographic guide.

3. The method according to claim 1, wherein the botulinum toxin type A is administered at a dose between 25 and 100 MU.

4. The method according to claim 1, wherein the botulinum toxin type A is administered at a dose of about 50 MU.

5. The method according to claim 1, said physiological solution contains about 0.9% sodium chloride.

6. The method according to claim 1, wherein said composition further comprises at least one aggregate selected from the group consisting of human albumin, sodium-based compounds, lactose and hydrochloric acid.

* * * * *

UNITED STATES PATENT AND TRADEMARK OFFICE

CERTIFICATE OF CORRECTION

PATENT NO. : 7,208,166 B2

APPLICATION NO. : 10/250486
DATED : April 24, 2007
INVENTOR(S) : Corrado Marchini et al.

It is certified that error appears in the above-identified patent and that said Letters Patent is hereby corrected as shown below:

Title Page, Item (54)
Title
"USE OF BOTULINE TOXIN TO OBTAIN A PRODUCT TO BE USED IN ARTICULAR PATHOLOGIES, PARTICULARLY COXARTHROSIS, EPICONDYLITIS AND ROTATOR MUSCLE CAP PATHOLOGY"

should read --USE OF BOTULINUM TOXIN FOR TREATMENT OF ARTICULAR PATHOLOGIES--

Signed and Sealed this

Twenty-sixth Day of February, 2008

JON W. DUDAS
*Director of the United States Patent and Trademark Office*

UNITED STATES PATENT AND TRADEMARK OFFICE

CERTIFICATE OF CORRECTION

PATENT NO. : 7,208,166 B2 Page 1 of 1
APPLICATION NO. : 10/250486
DATED : April 24, 2007
INVENTOR(S) : Corrado Marchini et al.

It is certified that error appears in the above-identified patent and that said Letters Patent is hereby corrected as shown below:

Title Page, Item (54) and Column 1, lines 1-5
Title
"USE OF BOTULINE TOXIN TO OBTAIN A PRODUCT TO BE USED IN ARTICULAR PATHOLOGIES, PARTICULARLY COXARTHROSIS, EPICONDYLITIS AND ROTATOR MUSCLE CAP PATHOLOGY"

should read --USE OF BOTULINUM TOXIN FOR TREATMENT OF ARTICULAR PATHOLOGIES--

This certificate supersedes the Certificate of Correction issued February 26, 2008.

Signed and Sealed this

Eighteenth Day of March, 2008

JON W. DUDAS
*Director of the United States Patent and Trademark Office*

UNITED STATES PATENT AND TRADEMARK OFFICE

CERTIFICATE OF CORRECTION

PATENT NO. : 7,208,166 B2
APPLICATION NO. : 10/250486
DATED : April 24, 2007
INVENTOR(S) : Corrado Marchini It is certified that error appears in the above-identified patent and that said Letters Patent is hereby corrected as shown below:

Title Page, Item (73)
Assignee "Societe de Conseils de Recherches et d'Applications Scientifiques SAS" should read --Societe de Conseils de Recherches et d'Applications Scientifiques SAS (S.C.R.A.S.)--

Signed and Sealed this

Fifth Day of August, 2008

JON W. DUDAS
*Director of the United States Patent and Trademark Office*